United States Patent [19]

Samain

[11] Patent Number: 5,655,552
[45] Date of Patent: Aug. 12, 1997

[54] PROCESS FOR THE PERMANENT RESHAPING OF KERATINOUS MATERIAL

[75] Inventor: Henri Samain, Bievres, France

[73] Assignee: L'Oreal, Paris, France

[21] Appl. No.: 475,648

[22] Filed: Jun. 7, 1995

[30] Foreign Application Priority Data

Jun. 30, 1994 [FR] France .................... 94 08068

[51] Int. Cl.$^6$ .................................. A45D 7/04
[52] U.S. Cl. .................. 132/205; 132/202; 132/203; 132/204; 424/702; 8/127
[58] Field of Search .................... 132/202, 203, 132/204, 205, 206; 8/127; 424/70.2; 427/342; 514/544

[56] References Cited

U.S. PATENT DOCUMENTS

| | | | |
|---|---|---|---|
| 3,533,417 | 10/1970 | Bartoszewicz | 132/204 |
| 3,860,446 | 1/1975 | Rushforth et al. | 427/342 |
| 4,066,392 | 1/1978 | Abel et al. | 8/127 |
| 4,660,580 | 4/1987 | Hoch et al. | |
| 4,793,993 | 12/1988 | Situa-Mangano | 424/70.2 |
| 4,795,629 | 1/1989 | Situa-mangano | 514/544 |
| 5,225,191 | 7/1993 | De Labbey | 132/204 |

FOREIGN PATENT DOCUMENTS

| | | |
|---|---|---|
| 0 512 879 | 11/1992 | European Pat. Off. |
| 0 114 414 | 8/1994 | European Pat. Off. |
| 41 17 858 | 12/1992 | France |

*Primary Examiner*—Gene Mancene
*Assistant Examiner*—Philogene Pedro
*Attorney, Agent, or Firm*—Finnegan, Henderson, Farabow, Garrett & Dunner, L.L.P.

[57] ABSTRACT

A process for treating keratinous material, in particular the hair, for the purpose of obtaining a permanent reshaping of the latter, in particular in the form of permanent-waved hair. The process includes the following steps: (i) a so-called "acidic composition" containing at least one carboxylic acid and/or one of the associated salts thereof is applied to the keratinous material to be treated, the pH of the acidic composition ranging from 2.5 to 7, (ii) the keratinous material thus treated is rinsed, (iii) a reducing composition containing at least one thiol is applied to the keratinous material thus rinsed, the keratinous material is placed under mechanical tension before, during or after the application of the reducing composition or before the application of the acidic composition, (iv) the keratinous material thus treated is then rinsed, (v) an oxidizing composition is applied to the keratinous material thus rinsed, (vi) and, finally, the keratinous material thus treated is rinsed again, the keratinous material being separated directly before or after the rinsing operation in step (vi) from the tension referred to above directly before or after the rinsing operation in step (vi).

26 Claims, No Drawings

PROCESS FOR THE PERMANENT RESHAPING OF KERATINOUS MATERIAL

The present invention relates to a process for treating keratinous material, in particular the hair, for the purpose of obtaining a permanent reshaping of the latter, in particular in the form of permanent-waved hair, the process being usable in particular in the field of professional hair salons, beauty salons, cosmetic salons and the like.

It is known that the most common technique for obtaining a permanent reshaping of the hair consists, in a first stage, in opening the keratin —S—S— disulphide (cystine) bonds using a composition containing a reducing agent (reduction step) followed, preferably after having rinsed the head of hair thus treated, in reconstituting, in a second step, the said disulphide bonds by applying to the hair, which has been placed under tension beforehand (rollers and the like), an oxidizing composition (oxidation step, also known as the fixing step) so as finally to give the hair the desired shape. This technique thus makes it equally possible either to make the hair wavy or to straighten it or to remove its curliness. The new shape given to the hair by a chemical treatment such as above is remarkably long-lasting and in particular resists the action of washing with water or shampoos, this being as opposed to simple standard techniques for temporary reshaping, such as hairsetting.

The reducing compositions which may be used in order to carry out the first step of a permanent-waving operation generally contain, as reducing agents, sulphites, bisulphites or thiols. Among the thiols, there may be mentioned cystine and the various derivatives thereof, cysteamine and the derivatives thereof, thiolactic acid, thioglycolic acid and the esters thereof, in particular glyceryl monothioglycolate, and thioglycerol.

As regards the oxidizing compositions required to carry out the fixing step, use is usually made, in practice, of compositions based on aqueous hydrogen peroxide solution or on alkali metal bromates.

A disadvantage of permanent-waving techniques known to date is that their repeated application to the hair can induce a gradual impairment in the quality of the hair over time, in particular as regards its sheen.

Another problem also lies in the fact that, for various reasons, it is generally necessary to buffer the pH of the thiol-based reducing compositions by addition of certain additives, and in particular carbonate-based products such as, for example, carbonic acid or carbon dioxide, ammonium or alkali metal carbonates or bicarbonates, primary, secondary or tertiary amine carbonates or bicarbonates, or organic carbonates, in particular such as guanidine carbonate. However, it turns out that the repeated application of the permanent reshaping operations using carbonate-based reducing compositions can result in a gradual and marked impairment of the cosmetic properties of the hair over time, in particular as regards the softness of the fibres, which tend to become increasingly coarse, and as regards their disentangling, the hair becoming increasingly difficult to disentangle. This impairment is, moreover, particularly pronounced when the fixing step of the permanent reshaping operation is carried out using a bromate.

The aim of the present invention is, in particular, to overcome the above-described disadvantages.

Even more precisely, the aim of the present invention is to propose a novel treatment process which is suitable for the permanent reshaping of keratinous material and which makes it possible to limit, or even to prevent, the degradation of the fibres by repeated permanent-waving treatments.

The aim of the invention is also to propose a process such as above which makes it possible to improve the cosmetic properties, in particular the softness and the ease of disentangling, of the fibres when they undergo a permanent reshaping treatment using a carbonate-based reducing composition, in combination with a fixing step, in particular using a bromate.

Thus, after considerable research conducted in this matter, the inventor has found that the application of certain acidic compositions to the hair before the application of the reducing composition could make it possible successfully to overcome the various drawbacks which are inherently associated with the repeated application to the hair of permanent-waving operations, especially of reducing compositions and in particular carbonate-based reducing compositions.

This discovery forms the basis of the present invention.

Now, it has been found by the inventor that these aims can be achieved successfully by applying an acidic composition to the hair before the application of the reducing composition thereto. This discovery forms the basis of the present invention.

Thus, the present invention now proposes a novel treatment process which is suitable for the reshaping and/or setting, in a permanent manner, of keratinous material, and in particular the hair, the said process being characterized in that it comprises the following steps:

(i) a so-called "acidic composition" containing at least one carboxylic acid and/or one of the associated salts thereof is applied to the keratinous material to be treated, the pH of the composition ranging from 2.5 to 7, (ii) the keratinous material thus treated is rinsed, (iii) a reducing composition containing at least one thiol is applied to the keratinous material thus rinsed, the means for placing the keratinous material under mechanical tension being implemented before, during or after the application of the reducing composition or before the application of the acidic composition, (iv) the keratinous material thus treated is then rinsed, (v) an oxidizing composition is applied to the keratinous material thus rinsed, (vi) and, finally, the keratinous material thus treated is rinsed again, the keratinous material being separated from the means for placing under tension referred to above directly before or after the rinsing operation in step (vi).

Other characteristics, aspects and advantages of the invention will emerge more clearly on reading the detailed description which follows, as well as the various concrete, but in no way limiting, examples intended to illustrate it.

Although the account which follows is essentially centred around the particular case of the treatment of hair, it will be noted here that the process according to the invention may be applied to any keratinous material in general, in particular eyelashes, moustaches, body hairs, wool and the like.

The term carboxylic acid is used in its broadest sense and preferably encompasses simple carboxylic acids, polycarboxylic acids and (poly)hydroxy(poly)carboxylic acids, which may obviously be taken alone or as a mixture.

By way of carboxylic acids which may be used in the compositions according to the invention, there may more particularly be mentioned lactic acid, tartaric acid, acetic acid, glycolic acid and citric acid.

According to a particularly preferred embodiment of the process of the present invention, the acid used is citric acid.

As mentioned above, it should be noted that the carboxylic acids used in the invention may be present, partially or totally, in the acidic composition, in the form of one of the associated salts thereof, this presence and its magnitude depending in particular on the final pH given to the said composition.

The pH of the acidic composition preferably ranges from 4 to 5.5 and may be adjusted using a base chosen, alone or as a mixture, from sodium hydroxide, potassium hydroxide, aqueous ammonia and primary, secondary or tertiary (poly) amines.

The (poly)amines may be chosen, alone or as a mixture, from monoethanolamine, diethanolamine, triethanolamine, isopropanolamine and 1,3-propanediamine or from polyamines corresponding to the formula:

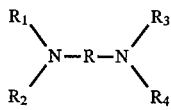

in which R is a propylene residue optionally substituted with a hydroxyl group or a $C_1-C_4$ alkyl radical and $R_1$, $R_2$, $R_3$ and $R_4$ represent, simultaneously or independently of each other, hydrogen or a $C_1-C_4$ alkyl or hydroxyalkyl radical.

Aqueous ammonia is preferably used.

After application of the acidic composition to the keratinous material and after optionally having left the keratinous material to stand, the keratinous material is rinsed and the reducing composition is then applied.

The concentration of carboxylic acid and/or of associated salts thereof generally ranges from 0.15 to 3N (normal), preferably from 0.3 to 1.5N.

The acidic composition may be in the form of a lotion, which may or may not be thickened, a cream, a gel, a shampoo, a conditioner or any other suitable form. It may contain cosmetic adjuvants known in particular for their hair application.

In accordance with the first step of the process according to the present invention (step (i)), the acidic composition is applied to the hair to be treated, which will preferably have been dampened beforehand. This application may be performed after the usual step of placing the hair under tension in a shape corresponding to the final shape desired for the hair (curls for example), it being possible for this step itself to be carried out by any means, in particular mechanical means, which is suitable and known per se for keeping hair under tension, for example such as rollers, curlers and the like.

The hair on which the acidic composition has been applied is then preferably left to stand for a period ranging from 30 seconds to 30 minutes, preferably from 30 seconds to 10 minutes.

The hair impregnated with the acidic composition is then rinsed, the rinsing operation generally being carried out with water.

In a third essential step of the process according to the invention, a reducing composition is applied to the hair, the reducing composition containing at least one thiol.

The thiol of the reducing composition may be chosen from thiols known as reducing agents such as, for example, thioglycolic acid, glyceryl monothioglycolate or glycol monothioglycolate, cysteamine and the $C_1-C_4$ acyl derivatives thereof such as N-acetylcysteamine or N-propionylcysteamine, cystine, N-acetylcystine, sugar N-mercaptoalkylamides such as N-(2-mercaptoethyl) gluconamide, 2-mercaptopropionic acid and derivatives thereof, thiolactic acid and esters thereof such as glyceryl monothiolactate, thiomalic acid, pantethine, thioglycerol, sulphites or bisulphites of an alkali metal or alkaline-earth metal, the N-(mercaptoalkyl)-ω-hydroxyalkylamides described in patent application EP-A-354,835, the disclosure of which is specifically incorporated by reference herein, and the N-mono- or N,N-dialkylmercapto-4-butyramides described in patent application EP-A-368,763, the disclosure of which is specifically incorporated by reference herein, the aminomercaptoalkylamides described in patent application EP-A-432,000, the disclosure of which is specifically incorporated by reference herein, the N-(mercaptoalkyl)succinamic acid derivatives or the N-(mercaptoalkyl)succinimide derivatives described in patent application EP-A-465,342, the disclosure of which is specifically incorporated by reference herein, the aminoalkylmercaptoalkylamides described in patent application EP-A-514,282, the disclosure of which is specifically incorporated by reference herein, and the mixture of 2-hydroxypropyl thioglycolate and 2-hydroxy-1-methylethyl thioglycolate described in patent application FR-A-2,679,448, the disclosure of which is specifically incorporated by reference herein.

Thioglycolic acid, thiolactic acid and 2-mercaptopropionic acid are preferably used.

The reducing agents mentioned above are generally present at a concentration ranging from 1 to 20% by weight relative to the total weight of the reducing composition.

The pH of the reducing composition generally ranges from 7 to 9.5 and preferably from 7.5 to 9.

The pH of the reducing compositions may conventionally be adjusted by addition of basifying agents such as, for example, aqueous ammonia, monoethanolamine, diethanolamine, triethanolamine, isopropanolamine, 1,3-propanediamine, carbonic acid or carbon dioxide, ammonium or an alkali metal carbonate or bicarbonate, a primary, secondary or tertiary amine carbonate or bicarbonate, or an organic carbonate such as guanidine carbonate, it obviously being possible for all these compounds to be taken alone or as a mixture. As mentioned above, one of the great advantages of the process according to the invention is that it is perfectly suitable in the case of carbonate-based reducing compositions. When used, the concentration of carbonate ion $CO_3^{2-}$ in the reducing composition generally ranges from 0.1 to 1.6M.

The reducing composition may be in the form of a lotion, which may or may not be thickened, a cream, a gel or any other suitable form and may contain additives known for their use in reducing compositions for the permanent reshaping of the hair.

The reducing composition may also be of the exothermic type, that is to say giving rise to some heating during the application to the hair, this providing a pleasant sensation to the person on whom the permanent-waving or the hair straightening is being performed.

The reducing composition may also contain a solvent such as, for example, ethanol, propanol or isopropanol or alternatively glycerol, generally at a maximum concentration of 20% relative to the total weight of the composition.

When the compositions are intended for an operation to straighten or remove the curliness from the hair, the reducing composition is preferably in the form of a thickened cream so as to keep the hair as stiff as possible. These creams are prepared in the form of "heavy" emulsions, based for example on glyceryl stearate, glycol stearate, self-emulsifiable waxes, fatty alcohols, etc.

It is also possible to use liquids or gels containing thickening agents such as carboxyvinyl polymers or copolymers which "stick" the hair together and keep it in the smooth position during the time of exposure to the composition.

Finally, the compositions may also be in a so-called "self-neutralizing" or alternatively "self-regulated" form and, in this case, the reducing agents used according to the invention are combined with at least one disulphide known for its use in a reducing composition for self-neutralizing permanent-waving.

Among such known disulphides, there may in particular be mentioned dithioglycolic acid, dithioglycerol, cystamine, N,N'-diacetylcystamine, cystine, pantethine, the N-(mercaptoalkyl)-ω-hydroxyalkylamide disulphides described in patent application EP-A-354,835, the disclosure of which is incorporated by reference herein, the N-mono- or N,N-dialkylmercapto-4-butyramide disulphides described in patent application EP-A-368,763, the disclosure of which is incorporated by reference herein, the aminomercaptoalkylamide disulphides described in patent application EP-A-432,000, the disclosure of which is incorporated by reference herein, the disulphides of the N-(mercaptoalkyl)succinamic acid derivatives or of the N-(mercaptoalkyl)succinimide derivatives described in patent application EP-A-465,342, the disclosure of which is incorporated by reference herein, and the alkylaminomercaptoalkylamide disulphides described in patent application EP-A-514,282, the disclosure of which is incorporated by reference herein. These disulphides are generally present in a molar ratio of from 0.5:1 to 2.5:1, and preferably from 1:1 to 2:1, relative to the reducing agent (see U.S. Pat. No. 3,768,490, the disclosure of which is incorporated by reference herein).

In accordance with the third step of the process (step (iii)), the compositions containing the reducing agent or agents as mentioned above are applied to the hair which has been pretreated with the acidic composition. This application may be performed before, during or after the usual step of placing the hair under tension.

Before performing the following rinsing step, the hair on which the reducing composition has been applied should, in a conventional manner, be left to stand for a few minutes, generally from 2 to 40 minutes, preferably from 5 to 30 minutes, so as to leave a good amount of time for the reducing agent to act properly on the hair. This waiting phase is generally carried out by leaving the treated hair to stand in the open air (room temperature). During this waiting phase, care is taken that the hair does not dry out completely and remains damp until the following step is carried out (to this end, bonnets or protective gels are possibly used, for example).

In the fourth step of the process (step (iv)), the hair impregnated with the reducing composition is then rinsed thoroughly, generally with water.

Next, in a fifth step (step (v)), an oxidizing composition is applied to the hair thus rinsed, with the aim of fixing the new shape given to the hair.

The oxidizing composition contains an oxidizing agent which may be chosen from aqueous hydrogen peroxide solution, an alkali metal bromate, a persalt or a polythionate. As mentioned above, one of the great advantages of the process according to the invention is that it is entirely suitable in the case of oxidizing compositions based on bromates. The concentration of bromates in the oxidizing composition generally ranges from 0.1 to 2M.

The pH of the oxidizing composition generally ranges from 2 to 10.

The oxidizing composition may contain cosmetic additives that are well known for this type of composition.

As in the case of the application of the reducing composition, the hair on which the oxidizing composition has been applied is then, in a conventional manner, left in a standing or waiting phase which lasts for a few minutes, generally from 3 to 30 minutes, preferably from 5 to 15 minutes.

The vehicle for the compositions used according to the invention (acidic composition, reducing composition and oxidizing composition) is preferably water or an aqueous-alcoholic solution of a lower alcohol such as ethanol, isopropanol or butanol.

Finally, in the last step of the process according to the invention (step (vi)), the hair impregnated with the oxidizing composition is rinsed thoroughly, generally with water. The keratinous material is separated from the tension means referred to in step (iii), directly before or after the rinsing operation.

A head of hair having good cosmetic properties is finally obtained: the hair is shinier, softer and easier to disentangle.

Concrete examples illustrating the invention will now be given.

EXAMPLE 1

Locks containing 8 g of Japanese hair were used. In order to sensitize them, they were bleached using a composition containing 20 volumes aqueous hydrogen peroxide solution to which is added, weight for weight, an alkaline lotion containing 2% of pure ammonia. The composition is left to act for 30 minutes. Bleached locks are thus obtained, which are used for the following tests.

Four permanent-waving processes are performed: three processes (Nos. 1, 2 and 3) with an acidic lotion applied at various phases of the process, and a process (No. 4) without acidic lotion.

The following compositions were used for these processes:

| Acidic lotion No. 1: | |
| --- | --- |
| citric acid | 10 g |
| 20% aqueous ammonia qs pH | 4.5 |
| oleocetyldimethyl-hydroxyethylammonium chloride | 0.4 g AM |
| demineralized water qs | 100 g |
| Reducing composition No. 1: | |
| thioglycolic acid | 8 g |
| ammonium carbonate | 6 g |
| 20% aqueous ammonia qs pH | 8.1 |
| demineralized water qs | 100 g |
| Oxidizing composition No. 1: | |
| sodium bromate | 7 g |
| phosphoric acid qs pH | 8 |
| demineralized water qs | 100 g |

The following permanent-waving processes were performed:

Process No. 1 (invention):

Acidic lotion No. 1 was applied to wet locks and, after an exposure time of 5 minutes, the hair was then rinsed. The locks thus treated were wound on 5 rollers 9 mm in diameter and reducing composition No. 1 was then applied to the hair thus wound; it was left to act for 15 minutes and the locks were then rinsed. Oxidizing composition No. 1 was next applied, it was left to act for 15 minutes and the hair was then rinsed. Finally, the hair was unwound from the rollers and then dried.

Process No. 2 (comparative)

A process similar to process No. 1 was carried out, the only difference being that the application of acidic lotion No. 1 is performed after the application of reducing composition No. 1.

Process No. 3 (comparative)

A process similar to process No. 1 was carried out, the only difference being that the application of acidic lotion No. 1 is performed after the application of oxidizing composition No. 1.

Process No. 4 (comparative)

A process similar to process No. 1 was carried out, but without applying acidic lotion.

The softness and the ease of disentangling of the locks treated with the various processes were evaluated by a panel of 12 judges.

The softness was rated from 0 to 5:

| 0 | very coarse hair |
| 1 | coarse hair |
| 2 | fairly coarse hair |
| 3 | fairly soft hair |
| 4 | soft hair |
| 5 | very soft hair |

The ease of disentangling was graded from 0 to 5:

| 0 | impossible to disentangle (the comb does not pass through) |
| 1 | very difficult to disentangle (about twenty combing sweeps are necessary to disentangle 8 g of hair) |
| 2 | difficult to disentangle (about ten combing sweeps are necessary to disentangle 8 g of hair) |
| 3 | fairly easy to disentangle (4 to 5 combing sweeps are necessary to disentangle 8 g of hair) |
| 4 | easy to disentangle (a single combing sweep is necessary) |
| 5 | very easy to disentangle (from the first combing sweep, the hair does not knot together) |

The averages of the ratings given were as follows:

| Process No. | Softness | Disentangling |
| --- | --- | --- |
| 1 (Invention) | 3.1 | 4 |
| 2 | 2.5 | 2.8 |
| 3 | 1.1 | 1 |
| 4 | 1.1 | 1.25 |

It was thus observed that the best softness and disentangling results are obtained by applying the acidic lotion before the reduction step.

EXAMPLE 2

Hair treated according to process No. 1 of Example 1 was shampooed (washing, rinsing and drying) 6 times and treatment process No. 1 of Example 1 was repeated.

Similarly, hair treated according to process No. 2 of Example 1 was shampooed (washing, rinsing and drying) 6 times and treatment process No. 2 of Example 1 was repeated.

As in Example 1, the softness and the ease of disentangling of the hair thus treated were evaluated; the following results were obtained:

| Process No. | Softness | Disentangling |
| --- | --- | --- |
| 1 (invention) | 3.0 | 3.8 |
| 2 | 1.1 | 1.5 |

It was thus observed that the difference in rating of softness and of disentangling was promoted in favour of the hair treated according to the invention.

EXAMPLE 3

Comparison of the pH of the acidic lotion

Process No. 1 was performed using two different acidic lotions: acidic lotion No. 1 (process No. 1) and acidic lotion No. 2 (process No. 1') which had the following characteristics were used:

| Acidic lotion No. 2: | |
| --- | --- |
| citric acid | 10 g |
| 20% aqueous ammonia qs pH | 9 |
| oleocetyldimethyl-hydroxyethylammonium chloride | 0.4 g AM |
| demineralized water qs | 100 g |

Processes No. 1 and No. 1' were carried out on the hair of three Japanese women, process No. 1 being applied on the left side, process No. 1' being applied on the right side.

As in Example 1, the softness of the hair thus treated was evaluated in the wet state. The softness and sheen of the hair were also evaluated once dry; the following results were obtained:

| Process No. | Softness wet hair | Softness dry hair | Sheen dry hair |
| --- | --- | --- | --- |
| 1 (invention) | 3 | 3 | 3.2 |
| 1' | 2.2 | 1 | 1.5 |

It was thus observed that the hair treated with an acidic lotion according to the invention (pH 4.5) had greater softness and sheen than those of hair treated with an acidic lotion (No. 1') having a different pH (pH 9).

EXAMPLE 4

Locks containing 8 g of European hair were used. In order to sensitize them, they were bleached twice using a composition containing 20 volumes aqueous hydrogen peroxide solution to which is added, weight for weight, an alkaline lotion containing 2% of pure ammonia. The composition is left to act for 30 minutes. Bleached locks are thus obtained, which are used for the following production example.

Process No. 1 was performed, but using an oxidizing composition which had the following characteristics:

| Oxidizing composition No. 2: | |
| --- | --- |
| aqueous hydrogen peroxide solution qs | 8 volumes |
| phosphoric acid qs pH | 3 |
| demineralized water qs | 100 g |

It was observed that the hair before drying is soft and easy to disentangle. Once dry, the hair is soft and shiny.

We claim:

1. A process for the permanent reshaping of keratinous material comprising the steps of:
   (i) treating a keratinous material by applying thereto an acidic composition containing at least one compound selected from carboxylic acid and the associated salts of carboxylic acid, the pH of said acidic composition ranging from 2.5 to 7;
   (ii) rinsing said treated keratinous material;
   (iii) applying a reducing composition containing at least one thiol to the rinsed keratinous material;
   wherein means for placing the keratinous material under mechanical tension are implemented before, during or after said application of said reducing composition or before said application of said acidic composition;
   (iv) rinsing the keratinous material thus treated in step (iii);
   (v) applying an oxidizing composition to the keratinous material rinsed in step (iv); and
   (vi) rinsing the keratinous material treated in step (v);
   and further wherein the keratinous material is separated, before or after the rinsing operation in step (vi), from said means for placing the keratinous material under tension.

2. The process of claim 1, wherein the at least one acid of the composition applied in step (i) is selected from simple carboxylic acids, polycarboxylic acids, and (poly)hydroxy (poly)carboxylic acids.

3. The process of claim 2, wherein said at least one acid is selected from lactic acid, tartaric acid, acetic acid, glycolic acid and citric acid.

4. The process of claim 3, wherein said at least one acid is citric acid.

5. The process of claim 1, wherein the pH of said acidic composition is adjusted using at least one base selected from sodium hydroxide, potassium hydroxide, aqueous ammonia and primary, secondary and tertiary (poly)amines.

6. The process of claim 5, wherein said polyamines correspond to the formula:

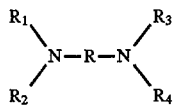

in which R is a propylene residue optionally substituted with a hydroxyl group or a $C_1$–$C_4$ alkyl radical and $R_1$, $R_2$, $R_3$ and $R_4$ represent, simultaneously or independently of each other, hydrogen or a $C_1$–$C_4$ alkyl or hydroxyalkyl radical.

7. The process of claim 5, wherein said (poly)amines are selected from monoethanolamine, diethanolamine, triethanolamine, isopropanolamine and 1,3-propanediamine.

8. The process of claim 5, wherein said base is aqueous ammonia.

9. The process of claim 1, wherein the concentration of said at least one compound in step (i) ranges from 0.15 to 3N.

10. The process of claim 9, wherein said concentration of said at least one compound in step (i) ranges from 0.3 to 1.5N.

11. The process of claim 1, wherein the pH of said acidic composition ranges from 4 to 5.5.

12. The process of claim 1, wherein before performing the rinsing operation (step (ii)), the keratinous material obtained from step (i) is left to stand.

13. The process according to claim 12, wherein said standing phase lasts from 30 seconds to 30 minutes.

14. The process according to claim 12, wherein said standing phase lasts from 30 seconds to 10 minutes.

15. The process of claim 1, wherein said at least one thiol of the reducing composition is selected from thioglycolic acid, thiolactic acid and 2-mercaptopropionic acid.

16. The process of claim 1, wherein said at least one thiol is present at a concentration ranging from 1 to 20% by weight relative to the total weight of the reducing composition.

17. The process of claim 1, wherein the pH of the reducing composition ranges from 7 to 9.5.

18. The process of claim 17, wherein the pH of the reducing composition ranges from 7.5 to 8.6.

19. The process of claim 1, wherein the reducing composition is a carbonate-based reducing composition.

20. The process of claim 19, wherein the reducing composition is carbonated using an additive selected from carbonic acid, carbon dioxide, ammonium and alkali metal carbonates and bicarbonates, primary, secondary and tertiary amine carbonates and bicarbonates, and organic carbonates.

21. The process of claim 20, wherein said additive is guanidine carbonate.

22. The process of claim 19, wherein the content of carbonate ion $CO_3^{2-}$ in the reducing composition ranges from 0.1 to 1.6M.

23. The process of claim 1, wherein the reducing composition additionally contains at least one disulphide, the reducing composition being of the self-neutralizing type.

24. The process of claim 1, wherein the oxidizing composition contains an oxidizing agent selected from aqueous hydrogen peroxide solution, an alkali metal bromate, a persalt and a polythionate.

25. The process of claim 24, wherein said oxidizing agent is an alkali metal bromate.

26. The process of claim 1, wherein said keratinous material is hair.

* * * * *